United States Patent
Jaffe et al.

(10) Patent No.: US 9,855,395 B2
(45) Date of Patent: Jan. 2, 2018

(54) PRESSURE BASED GAS LEAK TESTING

(75) Inventors: Michael Brian Jaffe, Cheshire, CT (US); Joseph Allen Orr, Park City, UT (US)

(73) Assignee: Koninklijke Philips N.V., Eindhoven (NL)

( * ) Notice: Subject to any disclaimer, the term of this patent is extended or adjusted under 35 U.S.C. 154(b) by 169 days.

(21) Appl. No.: 14/241,457

(22) PCT Filed: Sep. 10, 2012

(86) PCT No.: PCT/IB2012/054693
§ 371 (c)(1),
(2), (4) Date: Feb. 27, 2014

(87) PCT Pub. No.: WO2013/054217
PCT Pub. Date: Apr. 18, 2013

(65) Prior Publication Data
US 2014/0216451 A1    Aug. 7, 2014

Related U.S. Application Data

(60) Provisional application No. 61/533,987, filed on Sep. 13, 2011, provisional application No. 61/696,366, filed on Sep. 4, 2012.

(51) Int. Cl.
*G01L 13/00*    (2006.01)
*A61M 16/00*    (2006.01)
(Continued)

(52) U.S. Cl.
CPC .... *A61M 16/0051* (2013.01); *A61M 16/0003* (2014.02); *A61M 16/0833* (2014.02);
(Continued)

(58) Field of Classification Search
CPC ........... A62B 9/02; A62B 18/02; A62B 18/10; A62B 27/00; A61M 5/168; A61M 16/00;
(Continued)

(56) References Cited

U.S. PATENT DOCUMENTS

| 6,152,129 A | 11/2000 | Berthon-Jones |
| 7,775,207 B2 * | 8/2010 | Jaffe ................. A61M 16/0045 128/205.24 |
| 2014/0216451 A1 | 8/2014 | Jaffe et al. |

FOREIGN PATENT DOCUMENTS

| CN | 201060087 Y * | 5/2008 | .............. G01M 3/00 |
| CN | 201348557 Y | 11/2009 | |

(Continued)

OTHER PUBLICATIONS

English translation of abstract and claims of CN 201060087Y to Tong.*

*Primary Examiner* — Peter S. Vasat

(57) ABSTRACT

Gas-pressure-based testing, in some embodiments, features a self-leak-testing module (120) that includes an internal sensor and is configured for measuring, using the sensor, gas leakage (179, 180) from a set of walls that defines respective gas passageways that both exist within the module and are incident to the gas pressure measured. One or more walls of the set may extend outside the module. The module can be configured for deciding, based on a result of the measuring, whether a magnitude of the leakage exceeds a predetermined threshold. A source for applying the pressure may be internal (138) or external (104, 132, 135). Gas pressure based pattern recognition can be used to identify, optionally during treatment and in real time, one or more leak sites responsible for the leakage. The module is implementable as a ventilation monitoring module that measures differential flow of a breathing circuit, the testing serving to prevent cross-contamination of patients.

15 Claims, 3 Drawing Sheets

(51) Int. Cl.
*G01M 3/28* (2006.01)
*A61M 16/08* (2006.01)
*A61M 16/20* (2006.01)
*A61M 16/10* (2006.01)

(52) U.S. Cl.
CPC .... *A61M 16/0858* (2014.02); *A61M 16/0875* (2013.01); *A61M 16/20* (2013.01); *G01L 13/00* (2013.01); *G01M 3/2846* (2013.01); *A61M 2016/0027* (2013.01); *A61M 2016/0033* (2013.01); *A61M 2016/0036* (2013.01); *A61M 2016/103* (2013.01); *A61M 2205/15* (2013.01); *A61M 2205/3368* (2013.01); *A61M 2205/52* (2013.01); *A61M 2230/432* (2013.01)

(58) Field of Classification Search
CPC ...... A61M 16/08; A61M 16/12; A61M 16/20; A61M 2205/15; A61M 16/0833; A61M 16/0858; A61M 16/0875; A61M 2016/0027; A61M 2016/033; A61M 2016/0036; A61M 2205/52; G01L 13/00; G01L 13/04; G01L 13/06; G01L 15/00; G03M 3/00; G03M 3/26; G01M 3/2846; G01M 3/022

See application file for complete search history.

(56) References Cited

FOREIGN PATENT DOCUMENTS

| | | |
|---|---|---|
| EP | 0638793 A2 | 2/1995 |
| GB | 2396702 A | 6/2004 |
| JP | 2000121480 A | 4/2000 |
| JP | 2008232992 A | 10/2008 |
| KR | 20110007726 A | 1/2011 |
| WO | 9806449 A1 | 2/1998 |

\* cited by examiner

PRESSURE BASED GAS LEAK TESTING

CROSS-REFERENCE TO PRIOR APPLICATIONS

This application is the U.S. National Phase application under 35 U.S.C. §371 of International Application No. PCT/IB2012/054693, filed on Sep. 10, 2012, which claims the benefit of U.S. Provisional Patent Application No. 61/696,366, filed on Sep. 4, 2012, and U.S. Provisional Application No. 61/533,987, filed on Sep. 13, 2011. These applications are hereby incorporated by reference herein.

FIELD OF THE INVENTION

The present invention relates to pressure testing and, more particularly, to applying gas pressure in performing the testing.

BACKGROUND OF THE INVENTION

The measurement of proximal flow in the breathing circuit of a ventilating system in the critical care environment can often be challenging, particularly given the high humidity and secretions present and the length of mechanical ventilation that can last from days to weeks. Timing the start and end of the inspiratory and expiratory phases, for example, depends upon the observed flow speed in the breathing circuit between the patient's lungs and the ventilator gas flow generator.

Due to their robustness, differential pressure based flow sensors are often used in clinical environments. Differential pressure flow sensors incorporate some type of restriction (point orifice, variable flap, vena constriction, annular obstruction, target or linear flow restrictor) that generates a pressure difference across the sensor. Flexible tubing, attached to either side of the flow obstruction, transmits the differential pressure signal from the restriction located on the breathing circuit to a sensitive pressure sensor located inside a monitor, or monitoring module, at the bedside.

To maintain performance and function in this environment over time, differential pressure based respiratory measurement systems, implementable for example in the monitoring module, generally include zeroing and purging functions. Periodic zeroing, performed by exposing the two sides of the differential pressure sensors to the same pressure for a short period of time, is required. This is because pressure sensors drift due to both intrinsic and extrinsic factors including changes in temperature. High humidity in the breathing circuit often leads to condensation of moisture in the pressure transmission tubing eventually resulting in a damped and distorted pressure signal (e.g., reduced accuracy) if not cleared. Therefore, pressure transmission tubes are periodically purged with a source of gas (either air or inspiratory gas) to reduce the adverse effects of condensate on pressure and flow measurements.

The complexity associated with the valves and interconnections required for zeroing and purging functions has resulted in conventional respiratory measurement systems with "bulky", multi-piece designs, which are difficult to assemble due to many individual pneumatic connections.

Additionally, the number of connections between different components results in a greater potential for leaks at these interfaces.

SUMMARY OF THE INVENTION

The heightened risk of leakage in and from the ventilator monitoring module carries with it the possibility that an otherwise non-flowing body of gas in the flexible tubing, i.e., a pressure transmission tube, will be drawn into the module. The suctioning of this body of gas can occur as a result of the pressure drop created by the leakage at the module end of the tube. A possible consequence is that the module may pull in any nearby contamination that may exist in the tube and which originated from the patient's respiration. Cross-contamination could result, because, although the flow sensor and its transmission tubing are disposable, the module and its interface tubing are retained from patient to patient. In addition, synchrony of the inspiratory and expiratory phases can be upset unless extra leak compensation is performed.

What is proposed herein below is directed to addressing one or more of these concerns.

In an aspect of the present invention, a self-leak-testing module includes an internal sensor and is configured for measuring, using the sensor, gas leakage from a set of walls that defines respective gas passageways that both exist within the module and are incident to gas pressure measured in the measuring.

In a sub-aspect, at least one wall of the set extends outside the module.

In an additional sub-aspect, the module is configured for deciding, based on a result of the measuring, whether a magnitude of the leakage exceeds a predetermined threshold.

As another sub-aspect, the module includes a source for applying the pressure.

In a further sub-aspect, the module is configured for actuating the source for purging a pathway that extends from within the module from a passageway.

In a different sub-aspect, a self-leak-testing system includes, in addition to the module, an elongated duct releasably attachable, at one end, to connect to the module and, at the other end, capped so as to retain that pressure.

In an alternative sub-aspect, a self-leak-testing system includes the module and an external source of pressure.

As a further sub-aspect, the source is on a breathing circuit of a medical ventilating system.

In one more sub-aspect, a self-leak-testing system includes the module and a pressure transmission conduit extending from the module and defined by a wall of the set that extends outside the module.

In a further sub-aspect of this, the system is configured such that the gas pressure measured in the measuring exists within the conduit.

Among other further sub-aspects, the system includes a releasable attachment to the conduit as a source of the pressure.

Among other further sub-aspects, the conduit is received by the module via an input port of the module.

Among other further sub-aspects, the system is designed for monitoring treatment of medical patients and for retaining the conduit when switching to a next patient.

Among other further sub-aspects, the module includes a differential gas pressure sensor. The conduit is placed within the system, and configured, to afford input to the differential gas pressure sensor.

Among other further sub-aspects, the system is configured such that leakage of gas from the module in an operational, non-test mode of the module is operable to cause a body of gas in the conduit that would otherwise be non-flowing to be drawn into the module.

In a related sub-aspect, the module is configured such that the pressure measured in the measuring exists in a conduit received by the module at an input port of the module.

In a supplementary aspect, the module is configured for using pattern recognition to identify a location of the leak.

In a refinement, the module includes valves and is configured for the measuring from a different set of walls that is designated in accordance with respective different settings of the valves.

In one other sub-aspect, a ventilator monitoring module includes the above-described module.

In a related setting, a ventilator for a breathing circuit is configured with a test mode in which the ventilator, to test a ventilator monitoring module, applies pressure to a body of gas that is along and within an elongated portion, of the ventilator, that spatially defines the circuit along that portion.

In a more particular version, the module has internal plumbing and is configured for using the applied pressure in leak testing the plumbing.

Analogously, a computer readable medium embodies instructions executable by a processor for measuring, using a sensor, gas leakage from a set of walls that defines respective gas passageways that both exist within a module comprising the sensor and are incident to gas pressure measured in the measuring.

As a complementary method, building a leak-site-identification database involves:

iteratively performing the following:

a) creating a leak in a ventilator monitoring module that is configured for receiving gas but is not on a breathing circuit; and b) acquiring, for the database and for associating with said leak, signals representative of gas pressure applied to the module having the leak.

In yet another version of what is proposed herein, a monitoring device for a ventilating system includes at least one gas pressure sensor and is configured for monitoring gas leakage by performing, in real time during ventilating by the system, pattern recognition using, in real time, output of one or more of the sensors.

Details of the novel, gas-pressure-based module testing are set forth further below, with the aid of the following drawing, which is not drawn to scale.

DETAILED DESCRIPTION OF EMBODIMENTS

Figure 1:
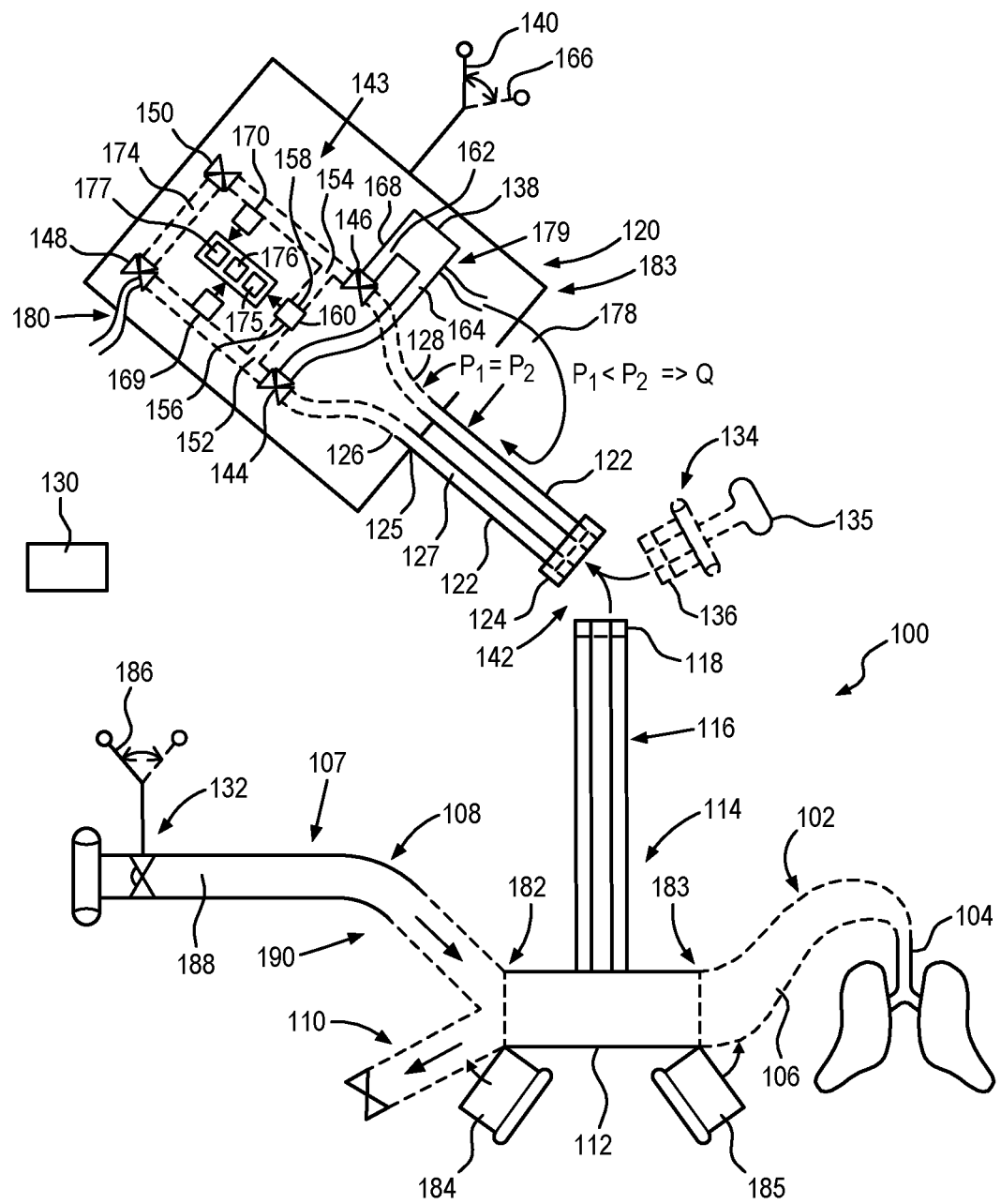
FIG. 1 is a schematic view of a ventilating system in accordance with and exemplary of the present invention.

FIG. 1 shows, by illustrative and non-limitative example, a medical ventilating system 100 affording gas-pressure-based module testing to prevent patient cross-contamination and to mitigate the amount of leak compensation required.

The ventilating system 100 includes, on a breathing circuit 102, a test lung 104, patient-side ducting 106, and a ventilator 107 comprising an inspiratory limb 108 and expiratory limb 110. It also includes, on the circuit 102, an airway adaptor 112 of a disposable flow sensor 114. The sensor 114, when capped at the adaptor end, serves as a releasably attachable elongated duct for leak testing purposes as discussed further below.

The ventilating system 100 includes, outside the breathing circuit 102 and extending from the adaptor 112, flexible tubing 116 of the flow sensor 114, terminated distally by a male connector 118. It further includes a self-leak-testing module implemented as a ventilator monitoring module 120. Also included, for joining the module 120 to the flow sensor 114, is a pair of flexible, pressure transmission conduits 122 that are terminated by a receptacle 124 for the male connector 118. The conduits 122 are respectively attached to a pair of input ports 125 of the module 120. The joining extends a pair of inner walls 126 that define a pathway 127 from the adaptor 112 into the module 120 to respectively define a pair of entry passageways 128 of the module 120. Although a flow sensor is shown in FIG. 1, a combination flow/$CO_2$ sensor may be used. The ventilating system 100 also has a microcontroller 130 in wireline or wireless communication with the module 120, with a pump 132 that is part of the ventilator 107, and with the test lung 104. In some embodiments, the ventilating system 100 features, as additional components, a leak test fixture 134 having gas pressure charging capability from a fixture pressure source 135 and/or a self-test plug 136 which relies on an existing pressure source 138, such as a pump or reservoir, of the ventilating system 100.

In an operational, non-test mode 140 of the ventilating system 100, shown in FIG. 1 with the conceptual lever rotated to the left, and in some test embodiments discussed further below, the flow sensor's connector 118 is inserted into the receptacle 124 to connect the flow sensor 114 to the module 120, thereby creating a flow sensor interface 142. The pressure transmission conduits 122, during patient ventilation by means of the breathing circuit 102, are pressure-wise in communication with the entry passageways 128.

Referring to the module's internal plumbing 143, each of the two entry passageways 128 encounters first a respective three-way differential-pressure valve 144, 146 and then a respective three-way zeroing valve 148, 150. Two, additional differential pressure input passageways 152, 154 extend toward respective inputs 156, 158 of a differential gas pressure sensor 160. Another two passageways 162, 164 deliver output gas pressure from the purge pump 138 serving, in a test mode 166, as a pressure source. Purging can be performed one conduit 122 at a time. The current gas path through the respective valve 144, 146, (i.e., through the passageway 162 defined by the respective wall 168 and the passageway 128 defined by the corresponding inner wall 126), directs a burst of gas outward onto the corresponding conduit 122 and carries it as far as the associated and defining inner wall 126 extends outside the module 120. The burst may be delivered during the patient's expiration phase so that any blocking material that is dislodged is not breathed in by the patient. During the burst, the other conduit 122 may afford access to its respective input 156, 158 of the differential gas pressure sensor 160, and can provide gas-pressure input information to other internal pressure sensors such as an absolute pressure sensor 169 or a gauge pressure sensor 170. The zeroing valves 148, 150 terminate, and can seal, the entry passageways 128 into the module 120; can, in another valve configuration setting, open the gauge pressure sensor 170 to the ambient atmosphere; and can, in a third setting, open a zeroing passageway 174 to connect the differential gas pressure sensor inputs 156, 158. The module's firmware resides in a Flash ROM 175. The module uses SRAM 176 for data storage and an EEPROM 177 to store system parameters.

The gas within the pressure transmission conduits 122 and flow sensor tubing 116 is ordinarily non-flowing 178, because the gas pressure is uniform along this path. $P_1$ and $P_2$ are two points along the path, the gas pressure being equal at the two points. The body of non-flowing gas in the path is stagnant, not flowing in the path in one direction or in the other, i.e., neither in the tubing-to-conduit nor the conduit-to-tubing direction.

The existence of a leak 179 due to a fault in the purge pump 138, a leak 180 due to a valve 148 being stuck in an open position, or leaks due to other causes such as eroded sealing surfaces, cracks, breaks in sensors 160, 169, 170 lowers 182 the gas pressure at point $P_1$ in relation to the gas pressure at point $P_2$, resulting in gas flow (Q) toward the module 120. Here, it is assumed that $P_1$ is further along the path in the tubing-to-conduit direction than is $P_2$. With leakage 179, 180 of sufficient magnitude, contaminants in the breathing circuit 102 could potentially reach the pressure transmission conduits 122 or the module 120. Since the module 120 and its conduits 122 are retained from patient to patient, there is the possible danger of cross-contamination. Gas loss from a single leak at a single site, or combination of leaks from different sites, in the module 120 and/or its conduits 122 can collectively result in a gas loss rate, or leakage 179, 180, that exceeds a predetermined threshold, i.e., is of sufficient magnitude such that initialization of the ventilating system 100 for the next patient can no longer continue and that, instead, some remedy such as equipment replacement or repair is needed.

A gas pressure decay test, as a kind of leak test, can make use of the purge pump 138 as a source of gas. The space being charged with gas includes at least one of the passageways 128, 152, 154, 162, 164, 174 for a given valve setting configuration. In effect, a set 183 of walls 126, 168 that defines respective gas passageways that both exist within the module 120 and are incident to the test-imposed pressure are walls that are checked collectively for gas leakage 179, 180 of sufficient magnitude. As a preliminary step, the self-test plug 136 is plugged into the receptacle 124 to seal it, as represented in FIG. 1 by the clockwise arrow. The charge is to a given pressure of, for instance, 100 centimeters (cm) $H_2O$. It is thereafter decided by the circuitry, e.g., in Flash ROM 175, that a leak exists in the module or its flow sensor interface 142, if, in accordance with the pressure decay test which is based on readings from the pressure sensors 169, 170, a downward change in pressure of at least a given amount occurs within a predetermined time period. For example, if the change is less than 10 cm $H_2O$ at the end of a 30 second time period, no leak is deemed to exist. An average pressure loss of 0.33 cm $H_2O$ per second, in the current example, can serve as a predetermined threshold for deciding to take remedial action, e.g., repairing or replacing equipment of the ventilating system 100 before treating the next patient. If the gas leakage exceeds the threshold, the ventilating system 100 notifies the operator of this determination. The notification can come by means of an audio or visual alert, or by some other sensory means. Gas pressure is measurable by, for example, the gauge pressure sensor 170. The charge can be delivered to, and by means of, one or both of the differential-pressure three-way valves 144, 146. The charge initially brings uniformity to the gas pressure throughout the space being charged, although any leak will lower pressure at the site of the leak.

An alternative to the self-test plug 136 is the flow sensor 114 with both ends 182, 183 of the adaptor 112 releasably sealed, as by means of respective removable, although tight fitting, caps 184, 185, to retain the applied pressure. By connecting the actual flow sensor 114 that will be used for the next patient, the actual interface 142 can be included in the leak test. This is an advantage over the self-test plug 136. However, the maximum gas pressure impossible is lower, on account of the interface 142.

Leak testing of the module 120 can, as an alternative to relying on an internal source of pressure, involve an external source of pressure, such as the pump 132 of the inspiratory limb 108. Only the patient-side cap 185 is applied. In a test mode 186 of the pump 132, it applies pressure to a body 188 of gas that is along and within an elongated portion 190, of the ventilator 107, that spatially defines the breathing circuit 102 along that portion. Alternatively, the leak test fixture 134 is usable instead of the flow sensor 114 and breathing-circuit pump 132, as indicated in FIG. 1, by the clockwise arrow. The leak test fixture 134, rather than serving as a plug, delivers a charge of gas from a source it contains or from a source 135 routed to it. The charge can be delivered to one or both conduits 122. The testing with an external source 104, 132, 135 of pressure can unintentionally be compromised by leakage from other than the module 120 and the conduits 122; yet, the more overall detection can be useful too, for relieving the overhead of leak compensation for example. Testing with an external source 104, 132, 135 of pressure can accordingly be supplemented with testing, as proposed herein, that uses an internal source 138 of pressure, or by ventilator leak testing that does not involve the module 120 and conduits 122.

Figure 2:
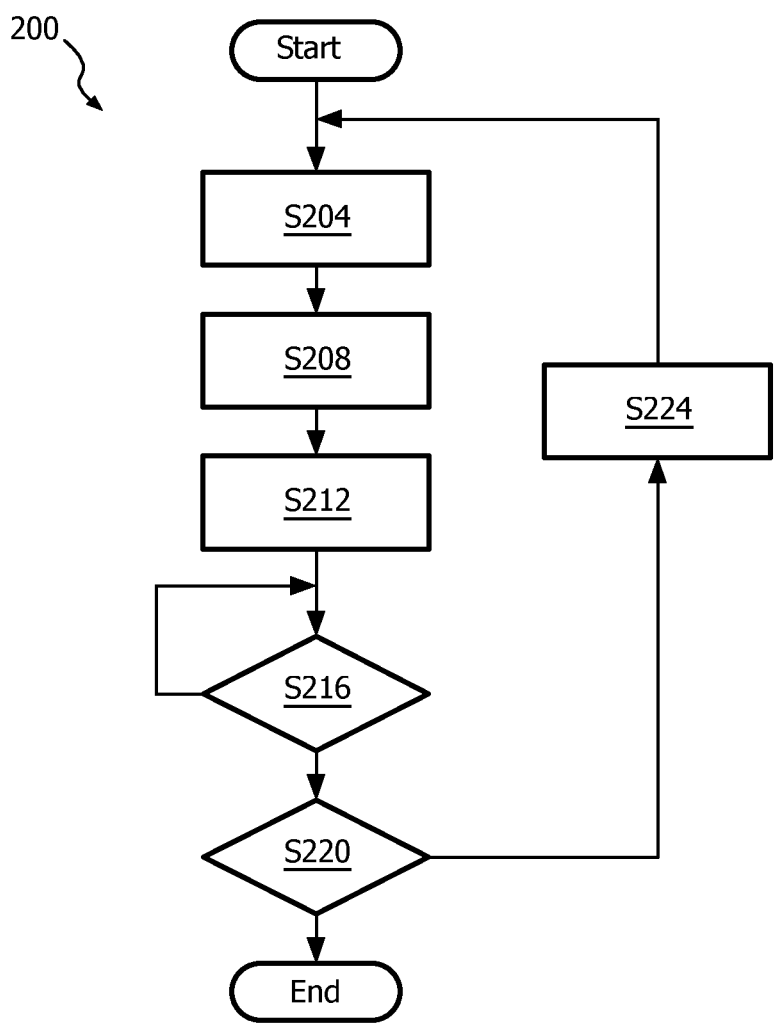
FIG. 2 is a flow chart of leak-site-identification database data acquisition in accordance with and exemplary of the present invention.

Pattern recognition can be used to identify a site of the leak 179, 180. FIG. 2 is an example of a leak-site-identification database data acquisition procedure 200 of a method for building a leak-site-identification database. The first step is to create a leak in a ventilator monitoring module (step S204). Alternatively or in addition, the leak can be created in one or both of the conduits 122 if, for example, a leak from the respective inner wall(s) 126 at the connector 118 is to be subject to the leak testing. This option would especially apply if and when the capped, disposable flow sensor 114 is attached for testing. Both the pressure transmission conduits 122 and attached module 120 are retained when switching from patient-to-patient. The database also contains examples of normal (non-leaking) signals. The module 120 for this iteration of the procedure 200 can be a new copy of the module or it can be the same module for which one or more leaks have already been created in one or more previous iterations. The next step is to apply gas pressure to a charge space of the module 120 (step S208). The charging pressure can be the same that is to be used during the leak test which is to be performed as part of every ventilator system initialization, the latter being performed whenever there is a switch from one ventilator patient to another. Any of the above-described methods can be employed to apply the charging pressure. In addition, the pressure can come from ventilating the test lung 104 under normal operating conditions; although, the data acquisition procedure differs from what immediately follows here, as discussed further below. When the pressure is applied (step S208), acquisition commences of gas pressure signals from one or more of the sensors 160, 169, 170, e.g., the differential gas pressure sensor 160 (step S212). This occurs under the operation of the Flash ROM 175 and SRAM 176, the signals being acquired being represented in FIG. 1 by means of the arrows. The acquisition is not limited to pressure sensor output, and may include the output of other sensors, such as temperature sensors. Acquisition occurs over a period of time whose length is the same as that used in leak testing. When the time period expires (step S216), and if acquisition is to continue for a new leakage scenario, i.e., with additional leaks to the same module 120 or with leaks in a new copy of the module (step S220), the module is provided (step S224), and the procedure 200 iterates, starting again at step S204.

The database of signals is then used to train an artificial neural network, or a look-up data set for a K-nearest neighbor, or other pattern-recognition algorithm. The trained artificial neural network encapsulates the pattern recognition-based leak-site-identification database. When in use for on-the-fly testing which is discussed further below, the acquired signals are compared against those of the stored database to determine whether the data best matches normal or leaking conditions and which leak condition best matches the acquired signals. Alternatively, for pressure decay testing performed during system initialization which prepares for switching to the next patient, i.e., testing which independently detects unacceptably high leakage 179, 180, comparisons involving normal examples in the pattern-recognition database to determine normal or leaking conditions are optional.

When the ventilating system 100 is being readied for treating a next patient, the database is queried, as part of the leak test during system initialization. The query is made while the applied gas pressure of the leak test decays and/or at timer expiration. Any leak sites identified can then be reported in an alert to the operator, especially if the leakage 179, 180 is deemed to be at an unacceptably high level. The magnitude and location of the leak may automatically be identified, and a statement as to continued use of the module 120 for that next patient could be made.

Figure 3:
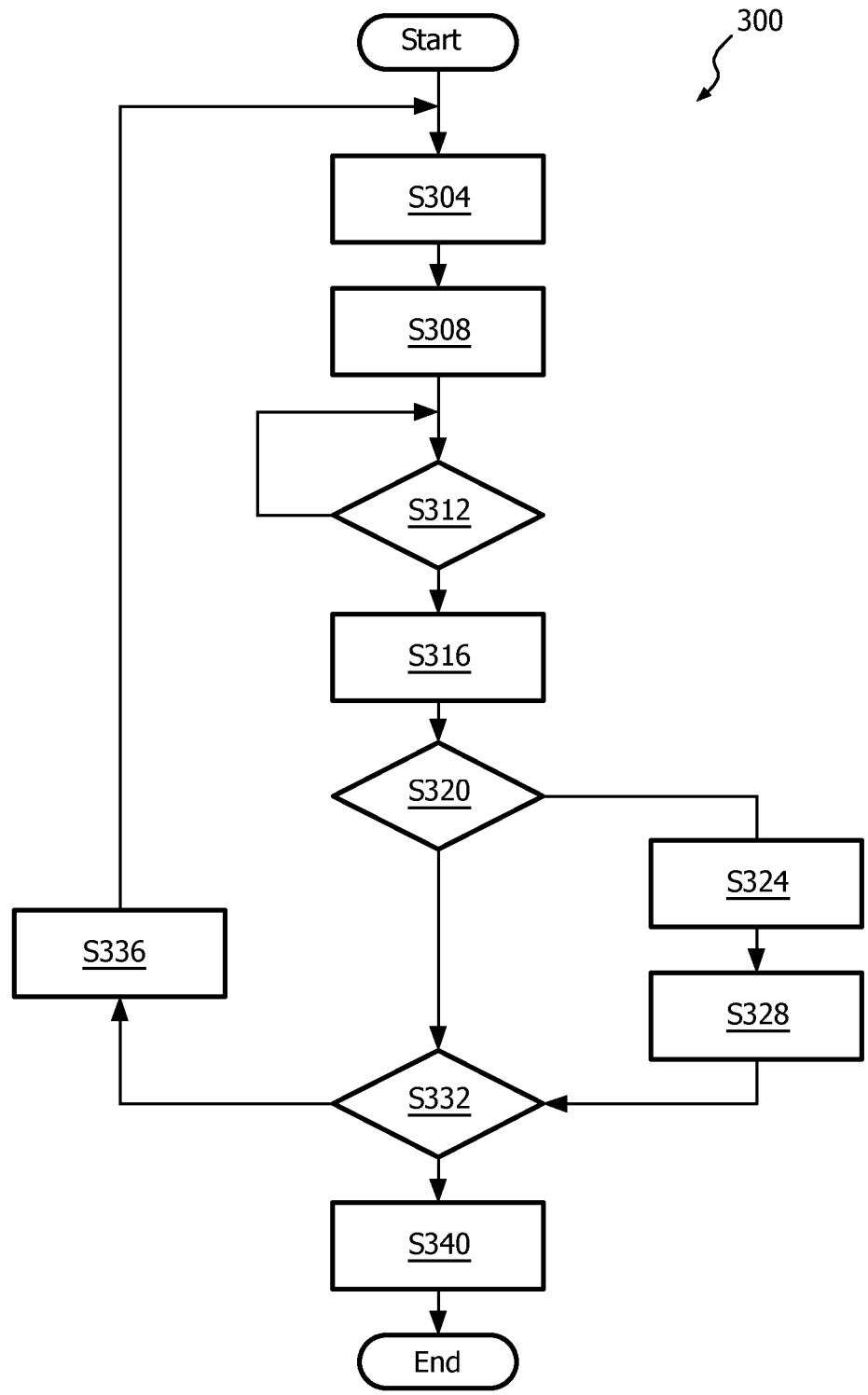
FIG. 3 is a flow chart of a leak test in accordance with and exemplary of the present invention.

One possible leak test procedure 300, utilizing a decay pressure test, is represented by FIG. 3. A "charge" space within the ventilating system 100 that includes the monitoring module 120 is charged with gas to a targeted pressure (step S304). The current charge space corresponds to a current valve-setting configuration. If the self-test plug is used, the ventilating system 100 automatically detects this and commences the gas charging. Other leak testing procedures may be started by operator actuation on a touchscreen or other operator input device. In any event, ongoing measurements of gas pressure by the sensors 160, 169, 170 may have commenced even by the time charging begins, and the measurements are recorded (step S308). When, for example, the charging timer in Flash ROM 175 expires at the end of the predetermined time period (step S312), the pressure readings just acquired at that time are compared to a predetermined, acceptability threshold (step S316). If an unacceptably high magnitude of leakage 179, 180 exists (step S320), the pattern recognition database is queried to match the current pressure readings to a particular one or more leak sites (step S324). The sites and magnitudes of the leaks, as well as the unacceptability of the module 120, are reported to the operator (step S328). The report may include instructions on how to proceed with preparing for the next ventilation patient. If the leak test is to be repeated with a different valve setting configuration that is, for example, designated by the operator or pre-programmed (step S332), one or more of the valves 144-150 are actuated to achieve the new setting (step S336) and the procedure 300 repeats, starting with the charging step S304. Otherwise, if the pressure test is not to be repeated with a different valve setting configuration (step S332), the leak test is complete, and the operator is notified of what remedial action to take, possibly including how to remove a system hold once the action has been carried out.

If the pattern recognition database has been built from data acquired using the test lung 104 as a pressure source, leak testing proceeds in an ongoing, or "on-the-fly", manner during patient treatment and without applying a pressure charge specifically for testing. A real-time-pattern-recognition-based monitoring device for the ventilating system 100 can be implemented as, for example, the monitoring module 120. The device includes at least one gas pressure sensor 160, 169, 170. It is configured for monitoring gas leakage by performing, in real time during ventilating by the system 100, pattern recognition using, in real time, output of the sensor(s) 160, 169, 170. It can be further configured for, in accordance with a result of the pattern recognition, notifying a user, optionally in real time, regarding the gas leakage monitored. If a pattern-recognition-based match occurs, this indicates the chance of leakage 179, 180 being great enough to raise the possibility of the module 120 being contaminated. The operator is consequently notified of the need to remedy the situation. If the notification is in real time, the operator can take immediate action, e.g., switching to a new module 120, if the remedy called for onscreen necessitates immediate equipment change or maintenance for the current patient being ventilated. The notification may be explicit, or the content onscreen may suggest the possibility of unacceptable leakage 179, 180. Particularly in the case of explicit notification, the operator's responsive input and/or remedial action may be required, in which case the operator may accordingly be automatically prevented from proceeding further, or again with ventilation for the next patient, until confirmation is received by the system 100 that the situation has been alleviated.

Gas-pressure-based testing, in some embodiments, features a self-leak-testing module that includes an internal sensor and is configured for measuring, using the sensor, gas leakage from a set of walls that defines respective gas passageways that both exist within the module and are incident to the gas pressure measured. One or more walls of the set may extend outside the module. The module can be configured for deciding, based on a result of the measuring, whether a magnitude of the leakage exceeds a predetermined, acceptability threshold. A source for applying the pressure may be internal or external. Gas pressure based pattern recognition can be used to identify, optionally during treatment and in real time, one or more leak sites responsible for the leakage. The module is implementable as a ventilation monitoring module that measures differential flow of a breathing circuit, the testing serving to prevent cross-contamination of patients.

While the invention has been illustrated and described in detail in the drawing and foregoing description, such illustration and description are to be considered illustrative or exemplary and not restrictive; the invention is not limited to the disclosed embodiments.

For example, the module may include a manifold of unitary construction, have connectors to the conduits 122 and serve as a housing for an electronic circuit board with the valves 144-150 and sensors 160, 169, 170.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A self-leak-testing ventilator monitoring module comprising:
an internal sensor;
internal valves;
pressure transmission conduits having a proximal end coupled to module input ports and a distal end of the pressure transmission conduits are terminated by a receptacle external to said self-leak-testing ventilator monitoring module, wherein the receptacle is configured for being releasably coupled to at least one of (i) a leak-test-fixture having a gas charging capability from a fixture pressure source, (ii) a self-test plug and (iii) a connector coupled at one end of flexible tubing of a disposable flow sensor, wherein an opposite end of the flexible tubing includes an airway adaptor configured for being coupled within a breathing circuit wherein the self-test plug and the disposable flow sensor rely on an existing pressure source for providing a gas charging capability;
gas passageways coupled between the internal sensor and the internal valves, and further coupled to said pressure transmission conduits; and
a microcontroller configured for controlling said self-leak-testing ventilator monitoring module between (i) an operational, non-test mode and (ii) a test mode, wherein the test mode includes the microcontroller controlling a gas pressure decay test in which the gas passageways are charged with gas to a test-imposed pressure, measuring, using said internal sensor, a change in pressure from the test-imposed pressure by at least a given amount within a predetermined time period sufficient for determining an existence or non-existence of gas leakage from a set of walls that defines respective gas passageways, and responsive to a determination of the existence of gas leakage, the microcontroller is further configured for providing a notification of the determination of the existence of gas leakage.

2. The module of claim 1, wherein the microcontroller is further configured for deciding, based on a result of said measuring, whether a magnitude of gas leakage exceeds a predetermined threshold.

3. A system comprising:
the self-leak-testing ventilator monitoring module of claim 1; and
the disposable flow sensor, wherein the flexible tubing comprises an elongated duct releasably attachable, at one end, via the connector, to connect to said self-leak-testing ventilator monitoring module and, at the other end, capped at open ends of the airway adapter so as to retain said test-imposed pressure.

4. A system comprising:
the self-leak-testing ventilator monitoring module of claim 1; and
an external pressure source of said test-imposed pressure.

5. The system of claim 4, wherein said external pressure source comprises a portion of a breathing circuit of a medical ventilating system.

6. A system comprising:
the self-leak-testing ventilator monitoring module of claim 1; and
a pressure transmission conduit extending from said self-leak-testing ventilator monitoring module and defined by a wall of said set that extends outside said self-leak-testing ventilator monitoring module.

7. The system of claim 6, wherein the leak-test-fixture having a gas charging capability from a fixture pressure source further comprises a releasable attachment for releasably coupling to said pressure transmission conduit, and wherein the fixture pressure source comprises a source of said test-imposed pressure.

8. The system of claim 6, further comprising a differential gas pressure sensor, wherein said pressure transmission conduit is placed within said system, and configured, to provide a gas pressure input to said differential gas pressure sensor.

9. The module of claim 1, wherein said test-imposed pressure exists in a pressure transmission conduit coupled to said self-leak-testing ventilator monitoring module at an input port of said self-leak-testing ventilator monitoring module.

10. The module of claim 1, wherein said microcontroller is further configured for using pattern recognition to identify a location of a leak interrelated to a source of said gas leakage determined above a threshold.

11. The module of claim 1, wherein the internal valves comprise a plurality of valves, wherein said microcontroller is further configured for said-measuring from a different set of walls that is designated in accordance with respective different settings of the plurality of valves.

12. A ventilator, comprising:
the self-leak-testing ventilator monitoring module of claim 1; and
a breathing circuit, wherein the self-leak-testing ventilator monitoring module is releasably coupled within said breathing circuit and configured for being operated in a test mode in which said ventilator applies a test-imposed pressure of gas that is along and within an elongated portion, of said ventilator, that spatially defines said breathing circuit along said portion.

13. The ventilator of claim 12, wherein said self-leak-testing ventilator monitoring module comprises internal plumbing and is further configured for using the applied test-imposed pressure in leak testing said internal plumbing.

14. A method for building a leak-site-identification database, said method comprising:
iteratively performing a sequence of acts, said sequence comprising the acts of:
a) creating a leak in one or more gas passageways of a self-leak-testing ventilator monitoring module according to claim 1, wherein the self-leak-testing ventilator monitoring module is configured for receiving gas but is not coupled within a breathing circuit;
b) acquiring, for said database and for associating with said leak, signals representative of gas pressure within the one or more gas passageways of said self-leak-testing ventilator monitoring module having said leak; and repeating the creating and acquiring for a desired number of further iterations using different leak and valve setting configurations.

15. A ventilating system, comprising:
the self-leak-testing ventilator monitoring module of claim 1, wherein the self-leak-testing ventilator monitoring module comprises at least one gas pressure sensor and is configured for monitoring gas leakage by performing, in real time during ventilating by said ventilating system, pattern recognition using, in real time, an output of one or more of said at least one gas pressure sensor.

\* \* \* \* \*